(12) United States Patent
Hershberger et al.

(10) Patent No.: US 7,976,545 B2
(45) Date of Patent: Jul. 12, 2011

(54) METHOD AND INSTRUMENTATION FOR PERFORMING MINIMALLY INVASIVE HIP ARTHROPLASTY

(75) Inventors: Troy W. Hershberger, Winona Lake, IN (US); Kimberly S. Parcher, Etna Green, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1240 days.

(21) Appl. No.: 11/030,020

(22) Filed: Jan. 5, 2005

(65) Prior Publication Data

US 2005/0234463 A1    Oct. 20, 2005

Related U.S. Application Data

(60) Provisional application No. 60/534,270, filed on Jan. 5, 2004.

(51) Int. Cl.
*A61B 17/00* (2006.01)
(52) U.S. Cl. .......................................................... 606/85
(58) Field of Classification Search .................. 606/79, 606/80, 85, 99, 84; 623/20.36; 411/385
See application file for complete search history.

(56) References Cited

U.S. PATENT DOCUMENTS

| | | | |
|---|---|---|---|
| 105,044 A | 7/1870 | Clark | |
| 152,776 A | 7/1874 | Stockwell | |
| 832,201 A * | 10/1906 | Kistler | 604/108 |
| 991,566 A | 5/1911 | Vernaz | |
| 1,111,657 A * | 9/1914 | Koehler | 411/385 |
| 1,178,310 A | 4/1916 | Getaz | |
| 4,306,550 A | 12/1981 | Forte | |
| 4,466,429 A * | 8/1984 | Loscher et al. | 606/180 |
| 4,468,149 A * | 8/1984 | Kelly et al. | 403/316 |
| 4,473,070 A | 9/1984 | Matthews et al. | |
| 4,549,319 A | 10/1985 | Meyer | |
| 4,601,289 A | 7/1986 | Chiarizzio et al. | |
| 4,706,659 A | 11/1987 | Matthews et al. | |
| 4,739,750 A | 4/1988 | Masse et al. | |
| 4,765,328 A | 8/1988 | Keller et al. | |

(Continued)

FOREIGN PATENT DOCUMENTS

DE          03801678 C1     8/1989

(Continued)

OTHER PUBLICATIONS

Berger, "Total Hip Arthroplasty Using the Minimally Invasive Two-Incision Approach," *Clinical Orthopaedics and Related Research*, vol. 417, 2003, pp. 232-241.

(Continued)

*Primary Examiner* — Eduardo C Robert
*Assistant Examiner* — David W Bates
(74) *Attorney, Agent, or Firm* — William F. Bahret

(57) ABSTRACT

Broaching instruments divided into multiple parts to reduce the size of incisions necessary to perform a total hip arhroplasty, minimizing trauma to tissue surrounding the hip joint. One approach is to divide the broach head into first and second segments for insertion through posterior and anterior incisions, respectively, and interconnection within the patient. Methods of preparing the proximal medullary canal of a femur for receiving a hip stem implant utilize the multi-part broaching instruments and two-incision techniques to introduce the broaching instruments into the patient for broaching the canal in preparation for receiving the implant.

39 Claims, 16 Drawing Sheets

U.S. PATENT DOCUMENTS

| | | | |
|---|---|---|---|
| 4,846,839 A | | 7/1989 | Noiles |
| 4,878,917 A | | 11/1989 | Kranz et al. |
| 4,921,493 A | | 5/1990 | Webb, Jr. et al. |
| 4,938,773 A | | 7/1990 | Strand |
| 5,006,121 A | | 4/1991 | Hafeli |
| 5,089,003 A | | 2/1992 | Fallin et al. |
| 5,108,437 A | | 4/1992 | Kenna |
| 5,169,402 A | * | 12/1992 | Elloy ............... 606/85 |
| 5,190,550 A | | 3/1993 | Miller et al. |
| 5,203,595 A | | 4/1993 | Borzone et al. |
| 5,342,366 A | | 8/1994 | Whiteside et al. |
| 5,441,501 A | | 8/1995 | Kenyon |
| 5,443,471 A | | 8/1995 | Swajger |
| 5,507,830 A | | 4/1996 | DeMane et al. |
| 5,607,431 A | | 3/1997 | Dudasik et al. |
| 5,704,940 A | | 1/1998 | Garosi |
| 5,713,905 A | | 2/1998 | Goble et al. |
| 5,766,261 A | * | 6/1998 | Neal et al. ............ 623/21.15 |
| 5,803,671 A | * | 9/1998 | Gray ............ 405/259.1 |
| 5,858,020 A | | 1/1999 | Johnson et al. |
| 6,090,146 A | | 7/2000 | Rozow, III et al. |
| 6,126,694 A | | 10/2000 | Gray, Jr. |
| 6,174,335 B1 | * | 1/2001 | Varieur et al. ............ 623/22.12 |
| 6,193,759 B1 | * | 2/2001 | Ro et al. ............ 623/23.28 |
| 6,238,400 B1 | * | 5/2001 | Bays ............... 606/96 |
| 6,238,436 B1 | | 5/2001 | Lob et al. |
| 6,428,578 B2 | | 8/2002 | White |
| 6,676,706 B1 | | 1/2004 | Mears et al. |
| 6,902,583 B2 | | 6/2005 | Gerbec et al. |
| 7,494,491 B2 | * | 2/2009 | Fankhauser et al. ............ 606/99 |
| 7,632,273 B2 | * | 12/2009 | Schnieders et al. ............ 606/79 |
| 7,799,029 B2 | * | 9/2010 | Jones ............... 606/53 |
| 2002/0040244 A1 | | 4/2002 | Despres, III et al. |
| 2002/0058999 A1 | | 5/2002 | Dwyer et al. |
| 2002/0059000 A1 | * | 5/2002 | Dwyer et al. ............ 623/22.43 |
| 2002/0099447 A1 | | 7/2002 | Mears et al. |
| 2002/0116067 A1 | | 8/2002 | Mears et al. |
| 2002/0151984 A1 | * | 10/2002 | White ............ 623/23.22 |
| 2003/0069605 A1 | * | 4/2003 | Bonutti et al. ............ 606/232 |
| 2003/0130741 A1 | | 7/2003 | McMinn |
| 2003/0149487 A1 | * | 8/2003 | Doubler et al. ............ 623/23.44 |

FOREIGN PATENT DOCUMENTS

| | | |
|---|---|---|
| DE | 04116507 C1 | 9/1992 |
| EP | 898100342 | 9/1989 |

OTHER PUBLICATIONS

Matta, "The Anterior Approach for Total Hip Replacement: Background and Operative Technique," HipandPelvis.com [on-line], © 2002-2003 [retrieved Dec. 31, 2003]. Retrieved from the Internet: http://www.hipandpelvis.com/physicians_corner/thr.htm. (2 pages).

Office Action, dated Apr. 1, 2009, in U.S. Appl. No. 11/030,019 (17 pages).

Office Action dated Apr. 14, 2009, in U.S. Appl. No. 10/912,644 (13 pages).

Office Action dated Sep. 5, 2007, in U.S. Appl. No. 10/912,644 (11 pages).

Office Action dated Nov. 4, 2009, in U.S. Appl. No. 10/912,644 (17 pages).

* cited by examiner

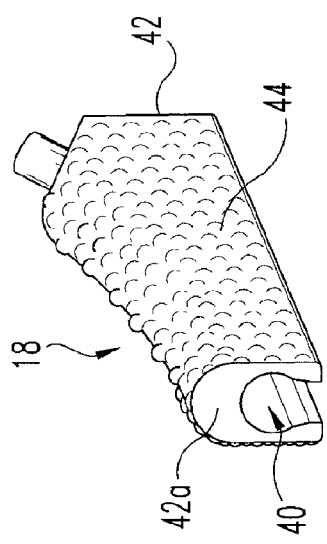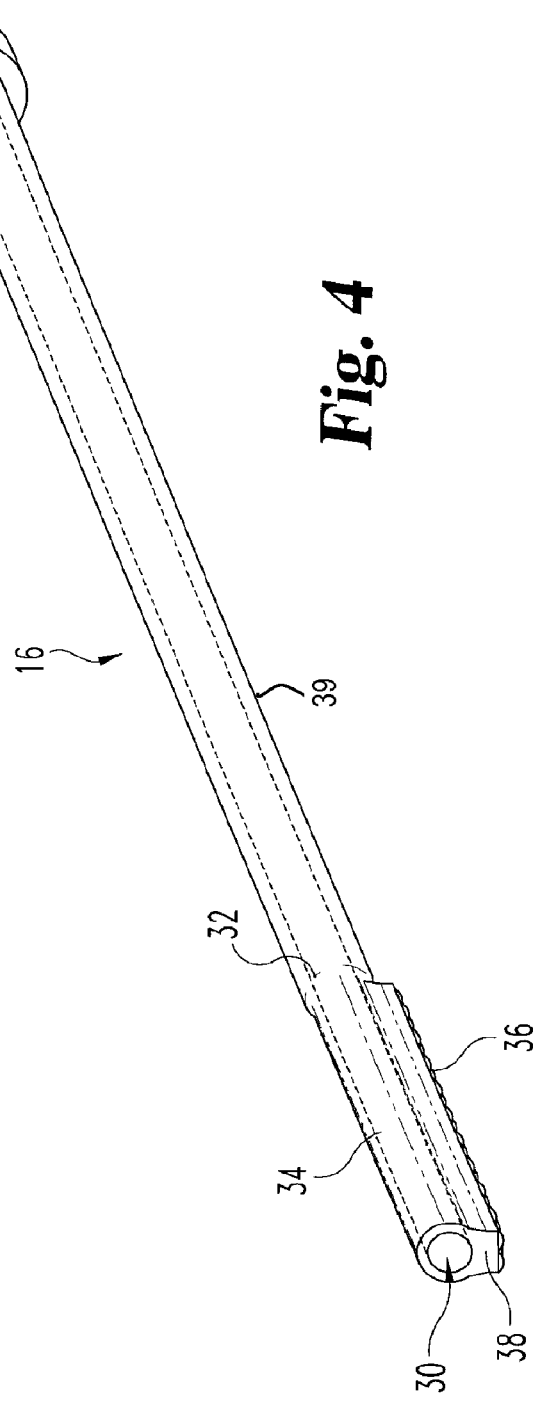

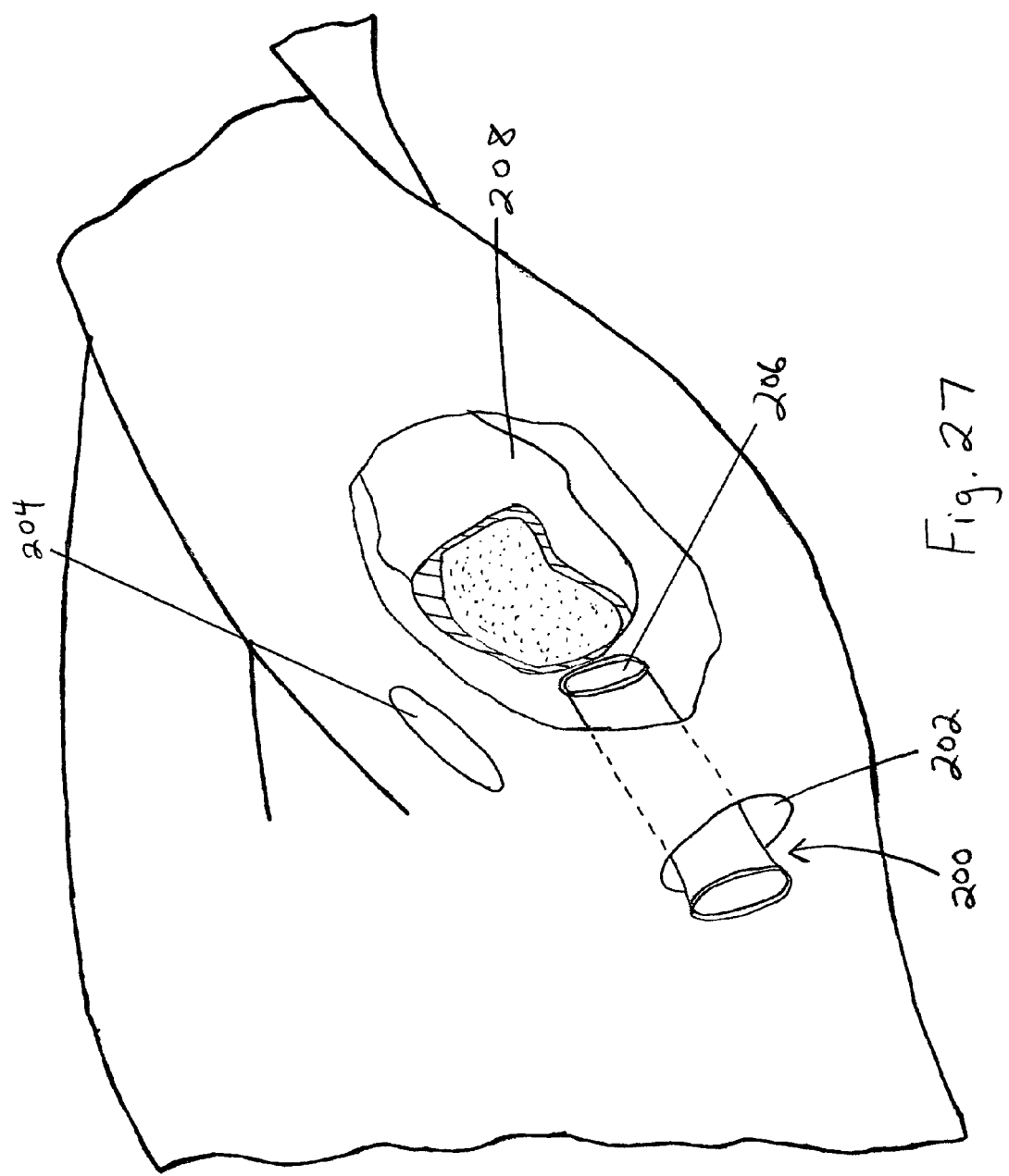

METHOD AND INSTRUMENTATION FOR PERFORMING MINIMALLY INVASIVE HIP ARTHROPLASTY

CROSS REFERENCE TO RELATED APPLICATIONS

This application claims the benefit of U.S. Provisional Patent Application No. 60/534,270, filed Jan. 5, 2004, and U.S. patent application Ser. No. 10/912,644, filed Aug. 5, 2004, both of which applications are hereby incorporated by reference, along with the following applications filed on Jan. 5, 2005: Ser. No. 11/031,197 and Ser. No. 11/030,019, both entitled Method And Instrumentation For Performing Minimally Invasive Hip Arthroplasty and filed in the name of Troy W. Hershberger.

BACKGROUND OF THE INVENTION

This invention relates to methods and instruments for performing hip arthroplasty, and more particularly to broach instruments and methods for preparing the proximal femur to receive a femoral implant as part of an implantable hip prosthesis.

In one popular method of performing a total hip arthroplasty through two incisions, the femur is prepared by passing instrumentation through a small posterior lateral incision. This posterior incision is similar to the incision made when performing a conventional femoral intramedullary nailing procedure except that the incision is located somewhat more superior. A second, anterior incision is made to facilitate the introduction of instrumentation for preparation of the acetabulum as well as to expose the femur from the anterior side. The surgeon is able to view the femur and resect the femoral head from this anterior side. Access along the femoral axis for reamers and broaches is most readily accomplished, however, through the posterior lateral incision. The surgeon bluntly divides the fibers of the gluteus maximus through the posterior incision to develop a small tunnel through which he may pass the femoral broaches, reamers and, eventually, the femoral implant. The femur is broached through the posterior lateral incision while the femur is viewed through the anterior incision.

There are disadvantages associated with the prior method and instrumentation described above. These include the necessity of making the posterior lateral incision large enough to accommodate passage of the full girth of the femoral broach and other instrumentation. Also, damage may be caused to the muscle fibers as well as the skin margins by excessive stretching of tissue and by repeatedly passing the broach and other instrumentation into and out of the posterior lateral incision.

SUMMARY OF THE INVENTION

The present invention offers significant advantages over prior devices and methods by providing, according to one aspect of the invention, a broach having a longitudinally split head for use in preparing the proximal medullary canal of a femur for receiving a hip stem implant. The longitudinally split broach head comprises lateral and medial broach segments that may be inserted separately, e.g., by inserting the lateral segment through a posterior incision and inserting the medial segment through a separate anterior incision. The broach segments have male and female coupling portions, and the broach head has a bore therethrough, e.g., for a reamer shaft or guide shaft. The split broach construction advantageously allows a reduction in the size of the incisions necessary to accommodate passage of the broach pieces and reduces the trauma to the gluteus muscles and other underlying tissue adjacent the femur.

According to another aspect of the present invention, a broach instrument having a longitudinally split broach head for use in preparing the proximal medullary canal of a femur for receiving a hip stem implant comprises a lateral broach segment and a medial broach segment, each having serrations along at least a portion thereof, and with the medial broach segment being longitudinally slidably engageable with a distal end of the lateral broach segment.

Another aspect of the present invention is a novel method of preparing the proximal medullary canal of a patient's femur using a multi-part broaching instrument with a first incision and a separate second incision adjacent a proximal end of a patient's femur. A first part of the multi-part broaching instrument is inserted through the first incision and a second part is inserted through the second incision. The first and second parts of the multi-part broaching instrument are interconnected within the patient and then used to broach the proximal medullary canal.

According to another aspect of the present invention, a broach instrument having a split broach head for use in preparing the proximal medullary canal of a femur for receiving a hip stem implant comprises first and second broach segments each having serrations along at least a portion thereof, and with the first broach segment being laterally engageable with the second broach segment and longitudinally fixed with respect to the second broach segment when engaged therewith.

Another novel method of broaching the proximal medullary canal of a femur in preparation for a hip stem implant in accordance with the present invention comprises inserting a broach head having an axial bore through an anterior incision adjacent a proximal end of a patient's femur. A guide shaft is inserted through a posterior incision adjacent the proximal end of the patient's femur and through the axial bore of the broach head. The guide shaft is advanced through the axial bore of the broach head and into the proximal medullary canal. The broach head is then moved along the guide shaft and into the proximal medullary canal.

The objects and advantages of the present invention will be more apparent upon reading the following detailed description in conjunction with the accompanying drawings.

BRIEF DESCRIPTION OF THE DRAWINGS

FIG. 3 is a perspective view of the medial broach segment.

FIG. 4 is a perspective view of the lateral broach segment.

FIG. 27 is a side view of a protective flexible sleeve used with the present invention.

DETAILED DESCRIPTION OF THE PREFERRED EMBODIMENTS

Figure 1:
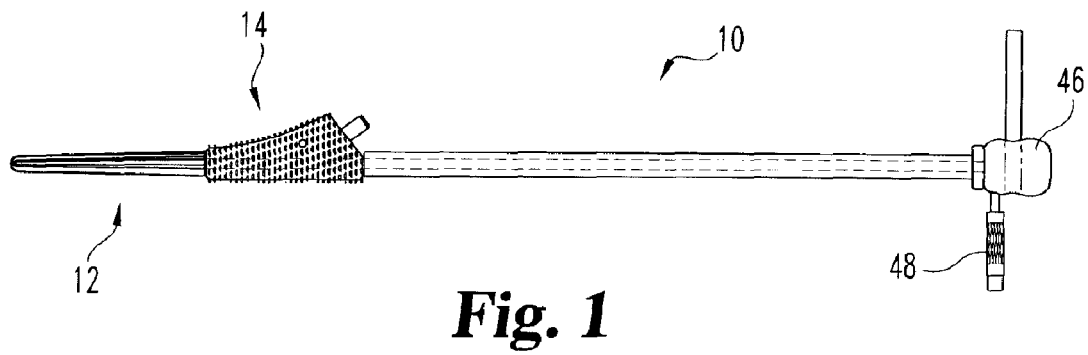
FIG. 1 is a side view of one embodiment of a broach instrument according to the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

It is desired to reduce the size of incisions necessary to perform a total hip arthroplasty in order to minimize trauma to the gluteus muscles and other underlying tissue adjacent the hip joint. According to the present invention, one approach to reducing the size of the incisions is to divide the broaching instrument used to broach the proximal medullary canal of the patient's femur into separate pieces that are each of smaller girth than the fully assembled broach instrument, allowing the size of the incisions necessary to accommodate passage of the broach pieces to be reduced. The multi-piece broach instrument may include a first broach head segment that may be inserted through a posterior incision adjacent the proximal end of the femur and a second broach head segment that may be inserted through a separate anterior incision. In certain applications the broach segments may be inserted sequentially through the anterior incision.

Figure 2:
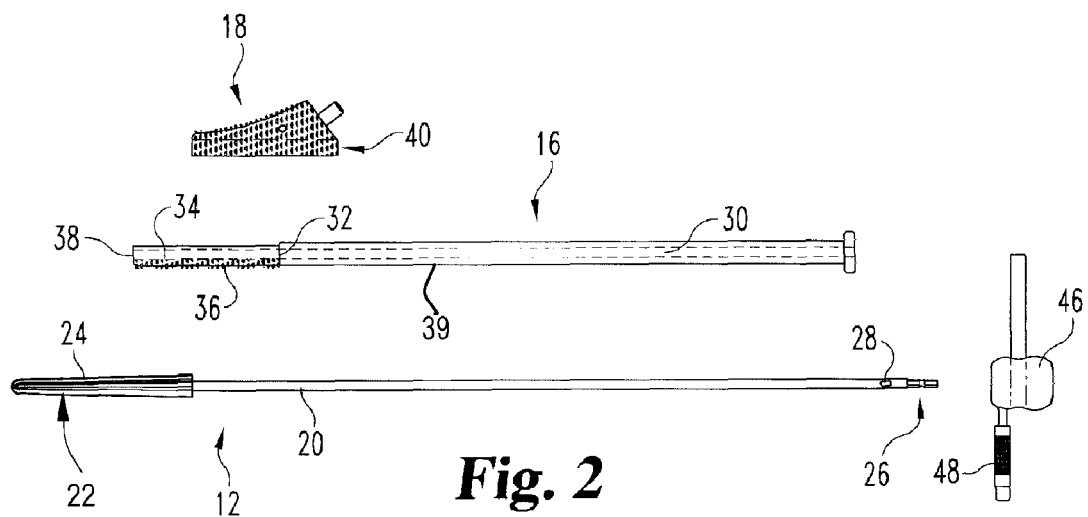
FIG. 2 is an exploded side view of the embodiment shown in FIG. 1.

In a first embodiment of the present invention shown in FIGS. 1 and 2, an instrument 10 for preparing the proximal medullary canal of a femur for receiving a hip stem implant generally comprises a reamer 12 and a broach head 14 having a lateral broach segment 16 and a medial broach segment 18.

The reamer 12 shown in FIG. 2 comprises a shaft 20, a cutting end 22 having plurality of flutes 24 and a driving end 26 having an aperture 28 therethrough proximate to the driving end 26. A shaft such as shaft 20 may be used as a guide shaft without a reamer on its distal end, but the first embodiment includes a reamer such as reamer 12 on the shaft such as illustrated in FIG. 2.

The lateral broach segment 16 shown in FIGS. 2 and 4 comprises an axial bore 30 for receiving the shaft 20 of the reamer 12, a shoulder portion 32 tapering into an adjoining male coupling portion 34, serrations 36 along a portion of the male coupling portion 34, and an abutting surface 38 for abutting against the flutes 24 of the reamer 12 during use. In the disclosed embodiment, the lateral broach segment 16 has a hollow shaft 39 integrally formed therewith. Alternatively, the male coupling portion 34 and serrations 36 may be a separate piece that may be threadedly engaged with the hollow shaft 39 and the male coupling portion 34 may not be continuous along the entire length of the serrations 36. As a further alternative, the lateral broach segment 16 may have the same outer diameter along its full length with a ring shaped stop about a portion of the lateral broach segment in place of the shoulder portion 32 to provide longitudinal support for the medial broach segment 18 during use.

The medial broach segment 18 shown in FIGS. 2 and 3 comprises a receiving slot 40, also referred to as a female coupling portion, an abutting surface 42 for seating against the shoulder 32 of the lateral broach segment 16 and a second abutting surface 42a for abutting against the flutes 24 of the reamer 12 during use. Serrations 44 are positioned about the outer surface of the medial broach segment 18.

Figure 7:
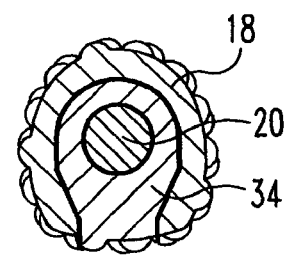
FIG. 7 is a cross sectional view of the lateral and medial broach segments assembled together.

In an alternative embodiment, the male and female coupling portions are formed on the medial and lateral broach segments, respectively. For example, the serrated sidewalls shown as part of the medial broach segment 18 in the cross-section of FIG. 7 may instead be formed on the lateral broach segment 16, thereby forming a slot, and a mating tubular appendage, such as male coupling portion 34, may be formed on the medial broach segment 18.

Figure 5:
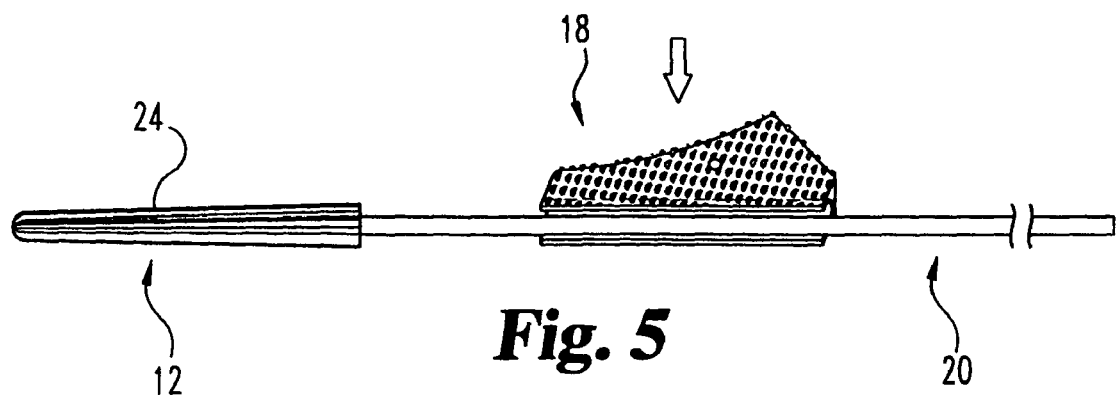
FIG. 5 is a side view of the medial broach segment adjacent the reamer prior to assembly.
Figure 6:
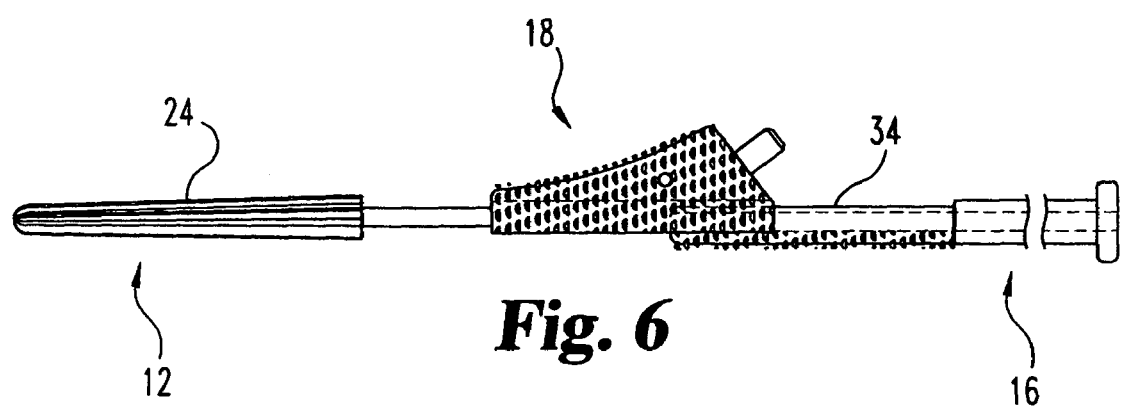
FIG. 6 is a side view of the lateral broach segment partially inserted into the medial broach segment.
Figure 8:
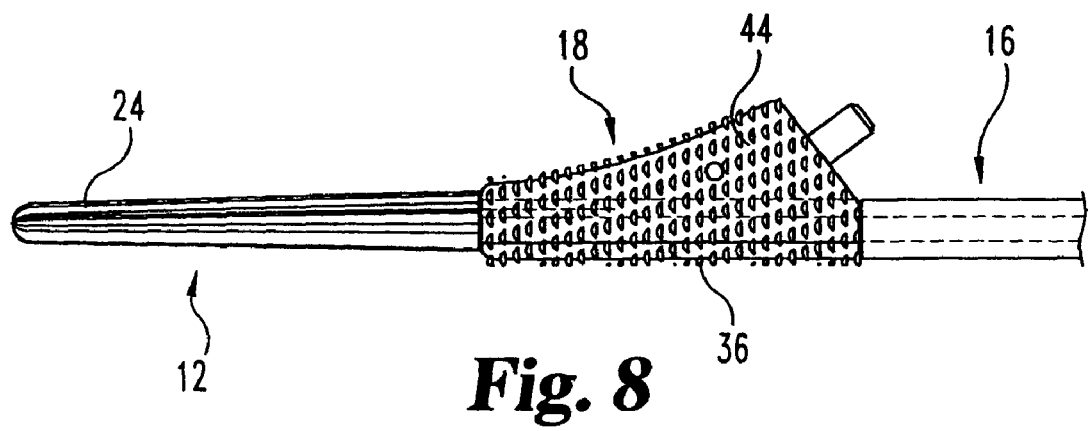
FIG. 8 is a side view of the broach segments fully assembled together.

The instrument 10 is assembled by interconnecting the broach segments 16, 18 on the reamer 12 as shown in FIGS. 5-8. The broach head tool 14 is preferably assembled about the reamer 12 by first laterally positioning the medial broach segment 18 adjacent the shaft 20 of the reamer 12 such that the receiver slot 40 surrounds the shaft 20 as shown in FIG. 5. The axial bore 30 of the lateral broach segment 16 is then axially aligned and slid over the shaft 20 as shown in FIG. 6. The male coupling portion 34 of the lateral broach segment 16 is then inserted within the receiver slot 40 of the medial broach segment 18 as shown in the cross sectional view of FIG. 7 and fully assembled as shown in FIG. 8.

Figure 9:
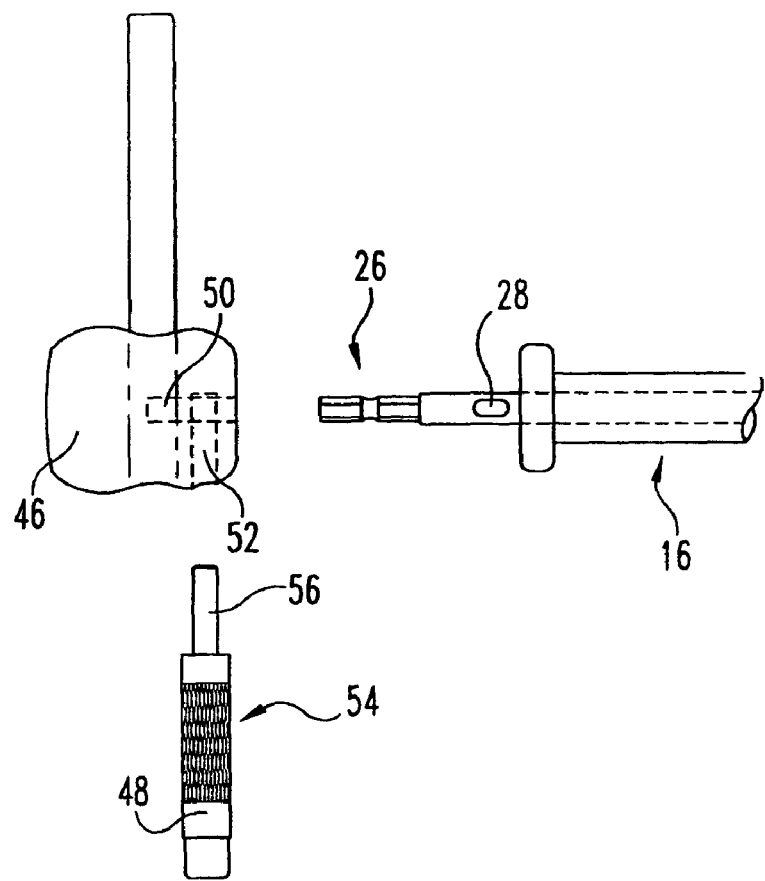
FIG. 9 is an exploded view of the impaction cap and handle of the instrument.

An impaction cap 46 and handle 48 as shown in FIG. 9 are used during the operation to hold the broach head 14 in place. The impaction cap 46 shown in FIG. 9 has a first aperture 50 for receiving the driving end 26 of the reamer shaft 20 and a second aperture 52 for receiving the handle 48. The handle 48 shown in FIG. 9 has a holding surface 54 for use during the broaching operation and a pin portion 56 sized and shaped to fit through the second aperture 52 of the impaction cap 46 and the aperture 28 of the reamer shaft 20 to connect the handle 48 to the impaction cap 46 and hold the instrument 10 together during use as shown in FIG. 13.

Figure 10:
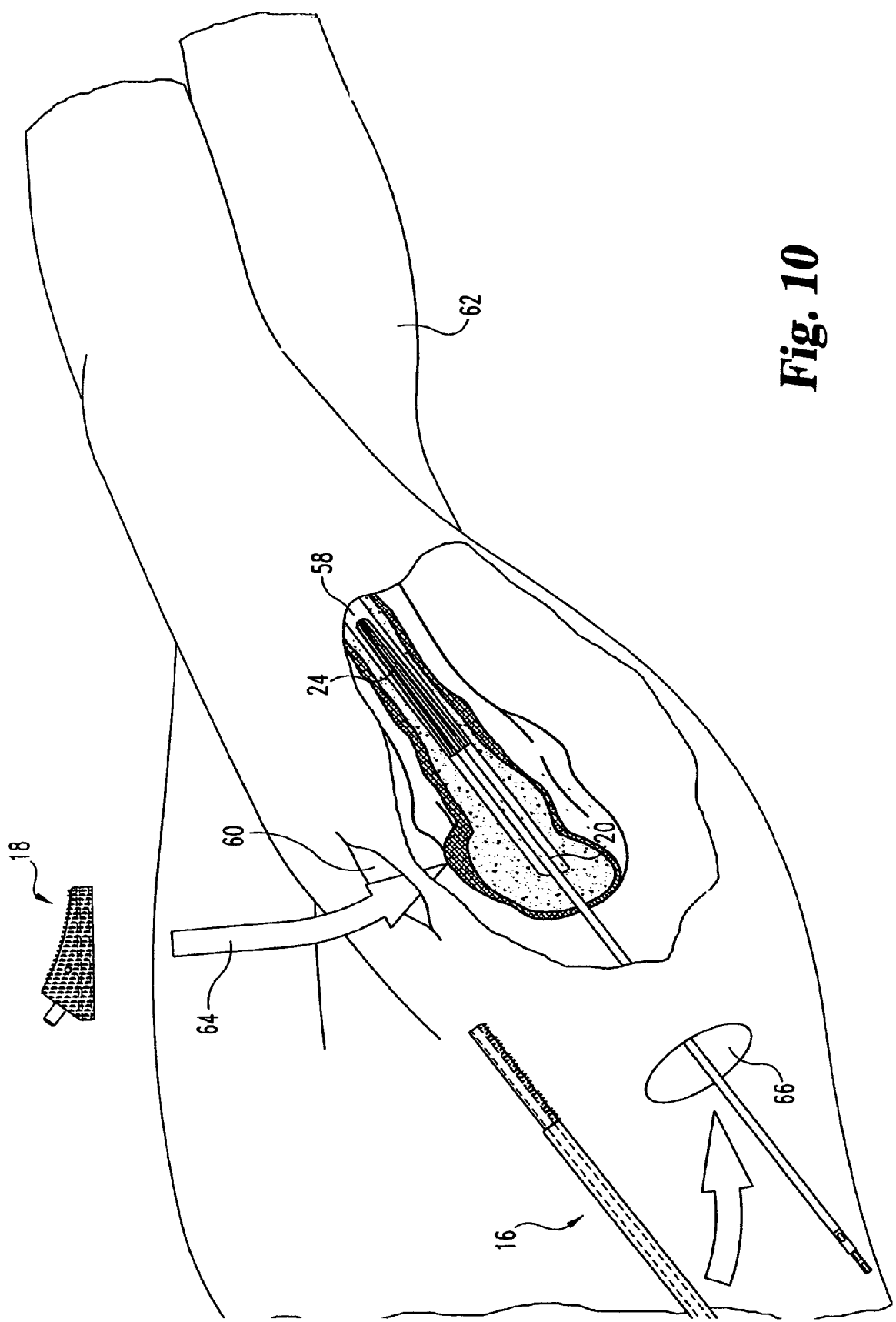
FIG. 10 illustrates use of the embodiment shown in FIG. 1 with a minimally invasive two-incision technique used in a total hip arthroplasty procedure.
Figure 11:
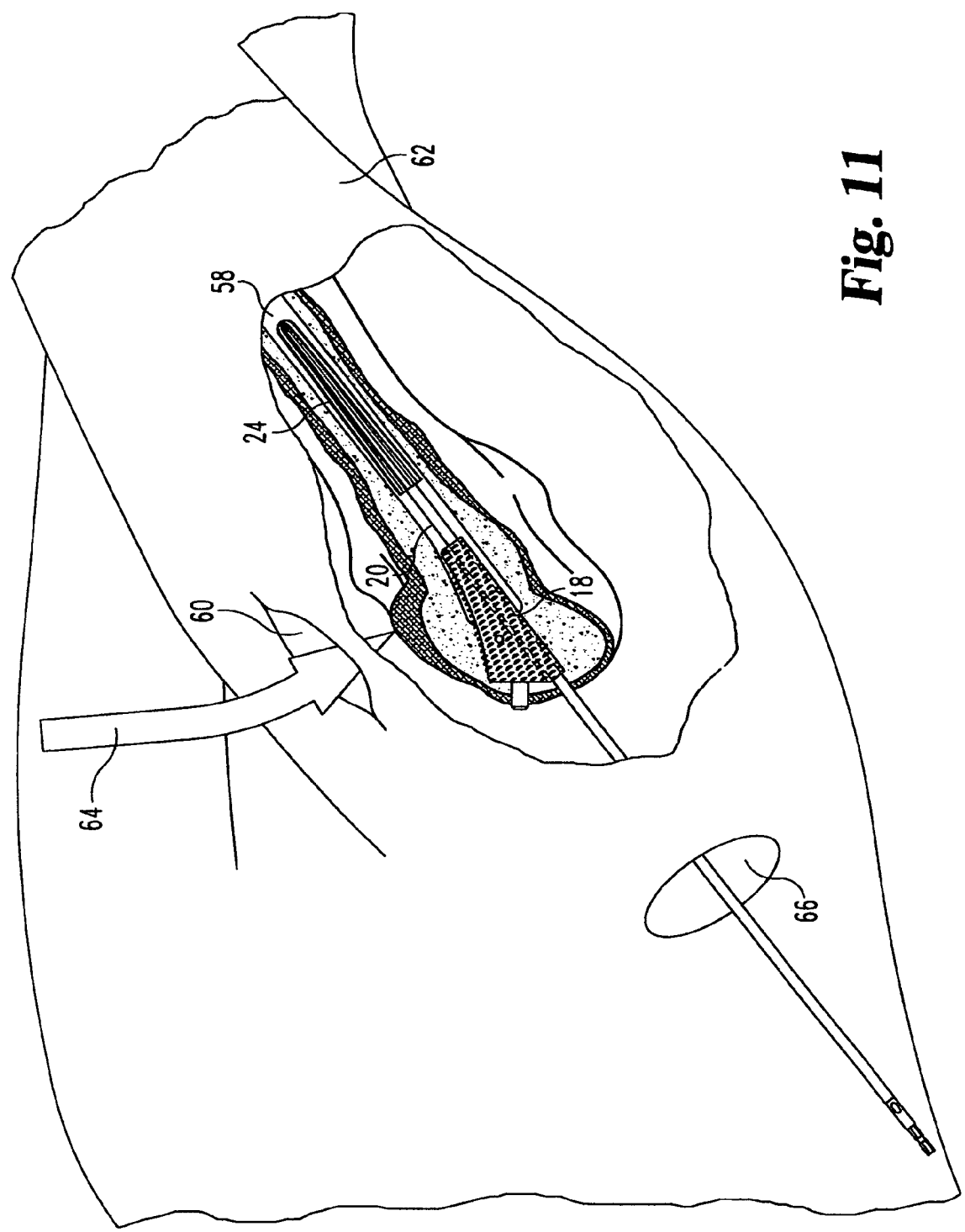
FIG. 11 illustrates insertion of the medial broach segment into the patient.
Figure 12:
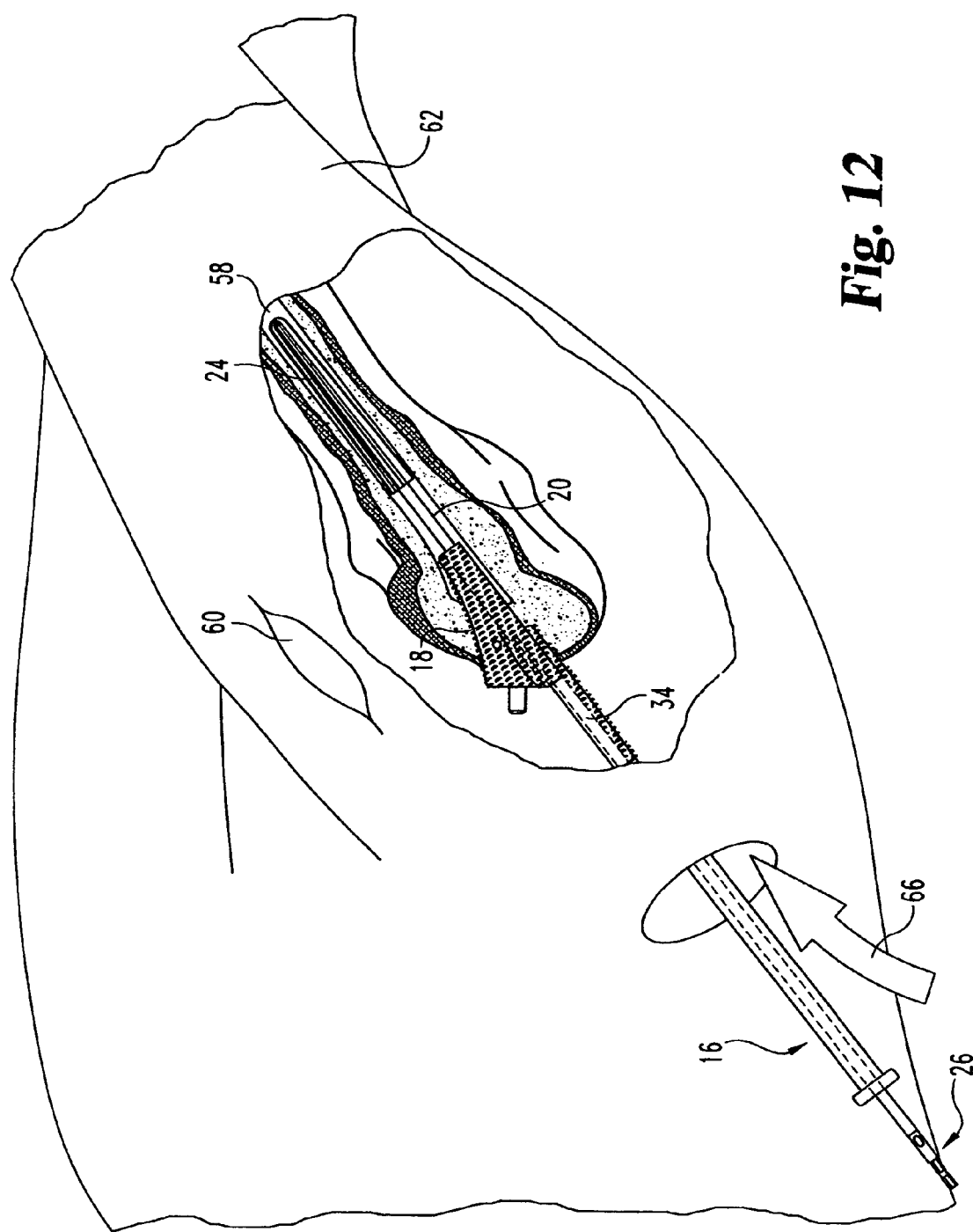
FIG. 12 illustrates assembly of the lateral and medial broach segments within the patient.
Figure 13:
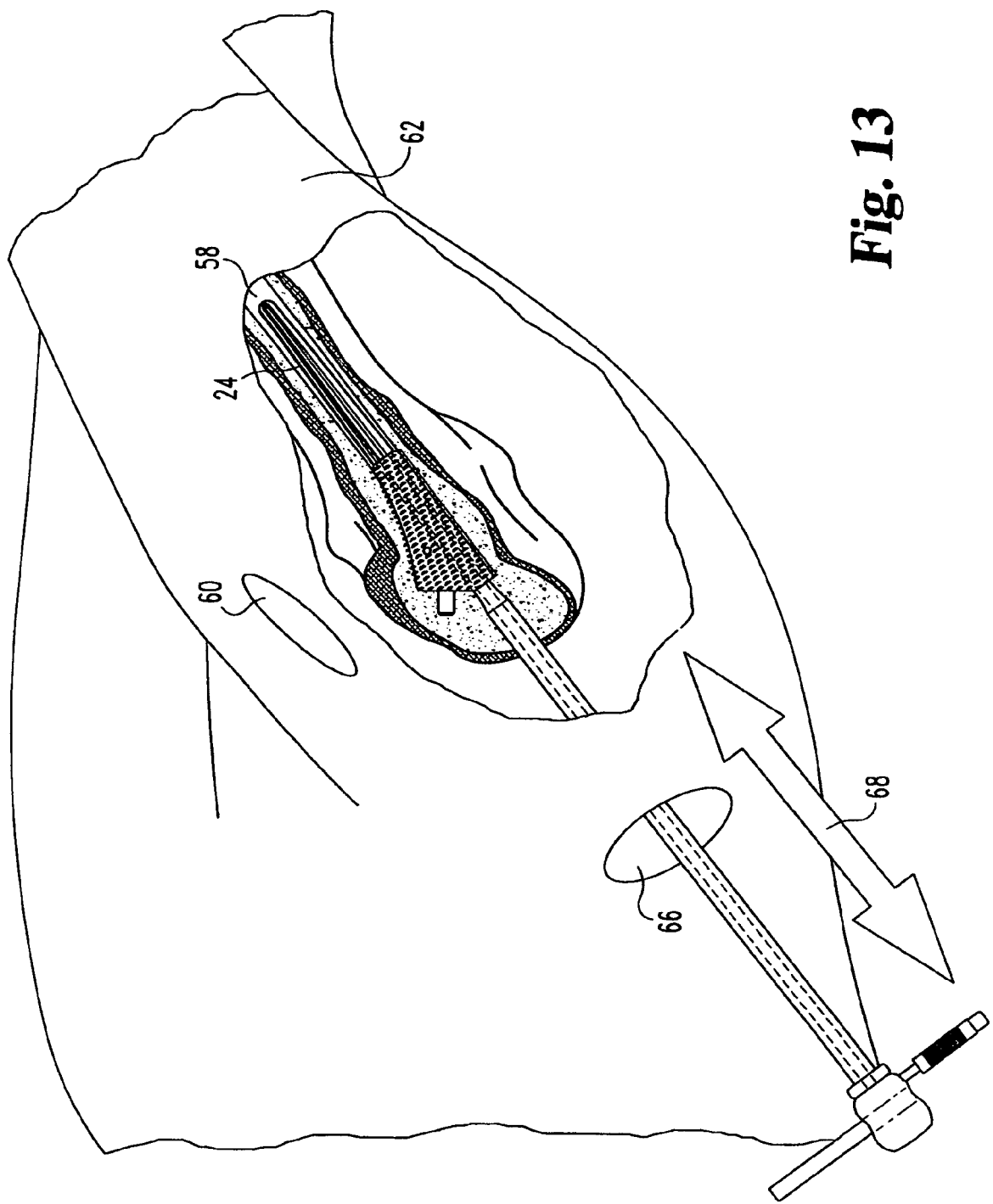
FIG. 13 illustrates use of the fully assembled instrument of FIG. 1.

The instrument 10 is assembled about the reamer 12 for preparation of the proximal medullary canal 58 as shown in FIGS. 10-13. FIG. 10 shows the general concept of inserting separate segments of the instrument through separate incisions within the patient. First, preferably, the medial broach segment 18 is inserted through the anterior incision 60 in the body of the patient 62 as designated by the arrow 64 and laterally positioned adjacent the shaft 20 of the reamer 12 such that the receiver slot 40 surrounds the reamer shaft 20 as shown in FIG. 11. Next, the lateral broach segment 16 is then preferably slid over the reamer shaft 20 through the posterior incision 66 in the body of the patient 62 as shown in FIG. 12 such that the male coupling portion 34 of the lateral broach segment 16 is inserted into the receiver slot 40 of the medial broach segment 18. Finally, the impaction cap 46 and handle 48 are then preferably assembled onto the end of the reamer shaft 20. FIG. 13 shows a completely assembled instrument 10 positioned within the proximal medullary canal 58 of a patient 62. The instrument 10 is then reciprocated generally in line with the double-headed arrow 68 to prepare the canal 58 for receipt of a hip stem implant.

When broaching is completed, the instrument 10 is preferably removed and disassembled in reverse order. First, preferably, the handle 48 and impaction cap 46 are removed from the end of the reamer shaft 20. Next, the lateral broach segment 16 is then preferably removed through the posterior incision 66. Next, the medial broach segment 18 is then preferably removed through the anterior incision 60. The lateral broach segment need be only partially withdrawn if further broaching is desired with a different size broach head, in which case the medial segment is replaced and the instrument is reassembled. Finally, at the completion of all desired broaching, the reamer 12 is then preferably removed through the posterior incision 66 of the patient 62.

Another embodiment of an instrument for preparing the proximal medullary canal of a femur for receiving a hip stem implant is shown in FIGS. 14-20. Instrument 70 generally comprises a first broach segment 72, a second broach segment 74, a broach handle 76, and a pusher rod 78.

Figure 14:
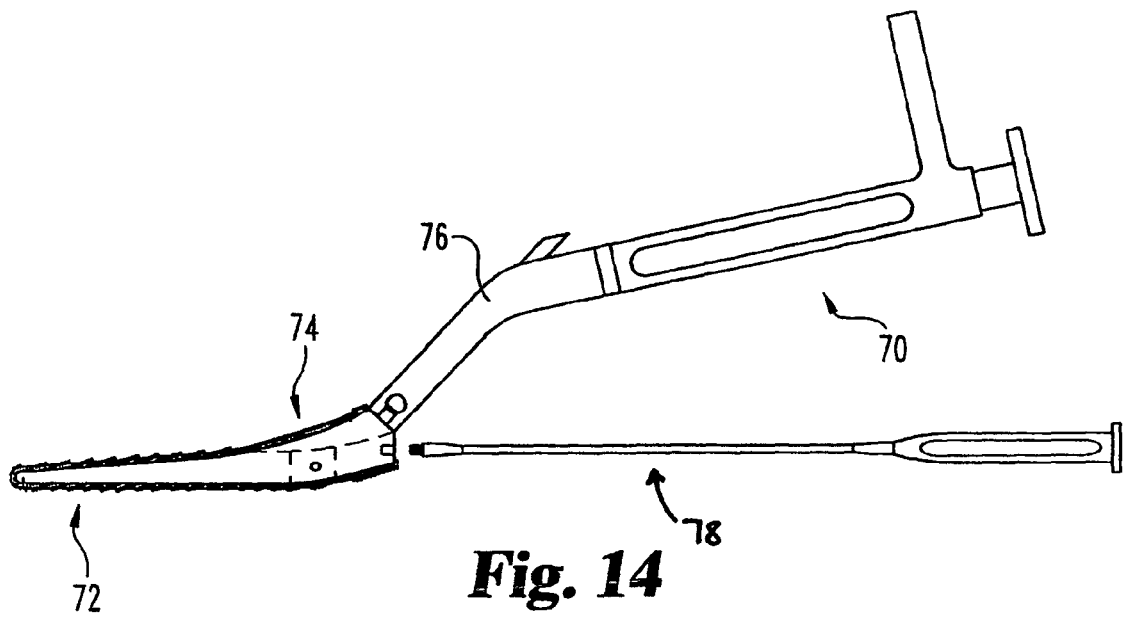
FIG. 14 is a partially exploded side view of another embodiment of a broach instrument according to the present invention.
Figure 15:
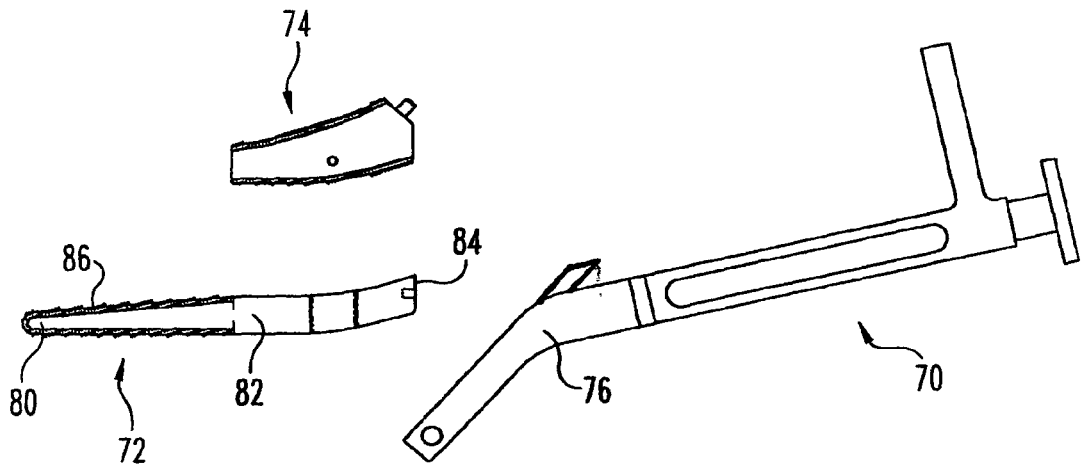
FIG. 15 is an exploded side view of the embodiment shown in FIG. 14.
Figure 16:
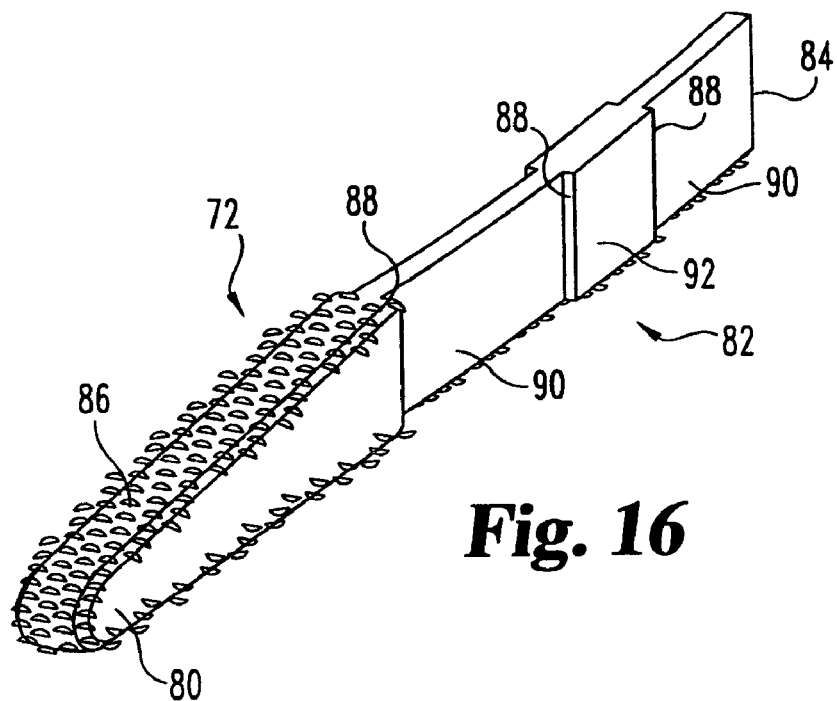
FIG. 16 is a perspective view of one broach segment in the embodiment of FIG. 14.

Broach segment 72 comprises a distal portion 80, a receiver portion 82 and a proximal end 84, with serrations 86 on distal portion 80 and elsewhere along the length of broach segment 72, as illustrated, for engaging the inner walls of the proximal medullary canal. The receiver portion 82 is generally defined by a pair of shoulders 88 that taper into an adjoining section 90 having a narrower cross sectional size. The receiver portion 82 has a retention feature, such as a rib 92 shown in FIG. 16, protruding outwardly to retain broach segment 74 in place during use. The proximal end 84 of broach segment 72 has a threaded aperture 94, as shown in FIG. 14, for receiving the pusher rod 78 during insertion and assembly of the instrument 70.

Figure 18:
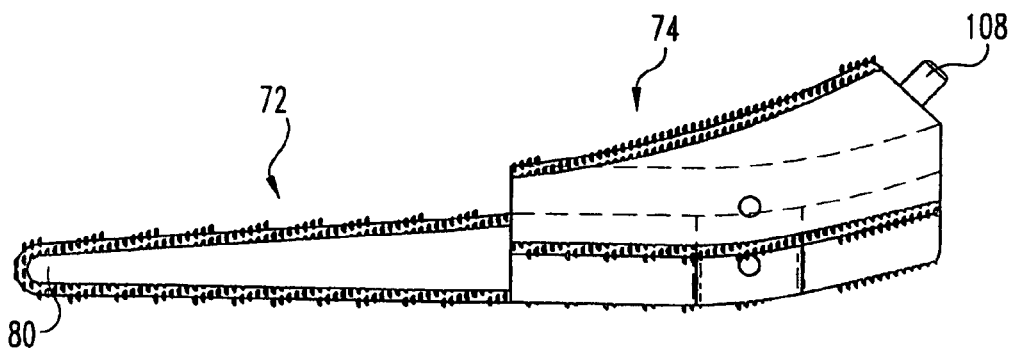
FIG. 18 is a side view of the broach segments partially engaged.
Figure 19:
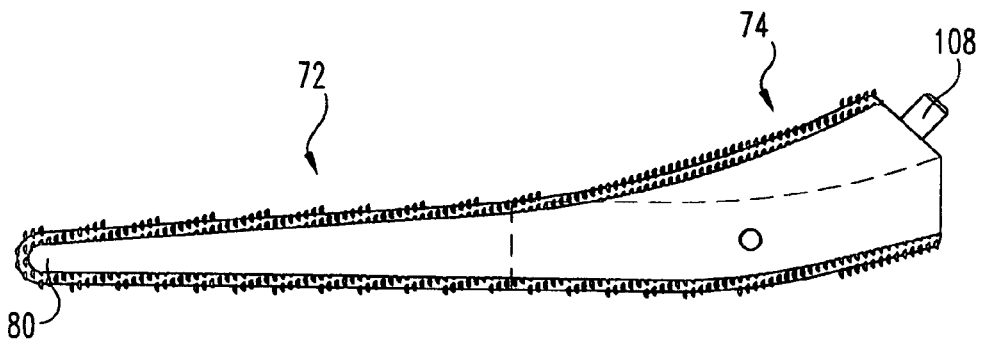
FIG. 19 is a cross sectional view of the broach segments assembled together.

Broach segment 74 comprises a receiver slot 96 having a first open end 98 defined by a proximal end 100 and a receiver seating surface 102 that seats against the top of the receiver portion 82 when broach segment 74 is assembled over broach segment 72 as shown in FIGS. 18 and 19. A retention groove 104 within the receiver slot 96 is sized and shaped to receive the rib 92 of broach segment 72. The proximal end 84 of broach segment 72 may be flush with the proximal end 100 of broach segment 74 as illustrated, or may be recessed within the open end 98 of broach segment 74, with the pusher rod 78 adapted to fit therein. Also, broach segment 74 extends more distally than broach segment 72 in the disclosed embodiment and thus may be viewed as the distal segment, but in alternative embodiments it may have the same length as segment 72.

Figure 17:
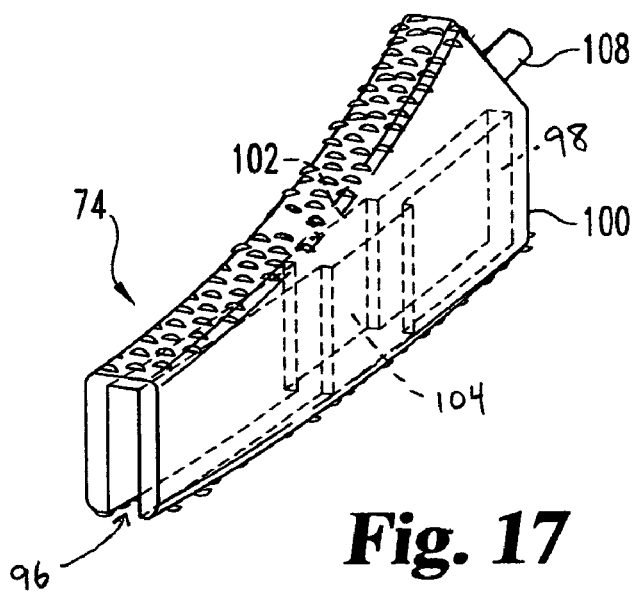
FIG. 17 is a perspective view of another broach segment in the embodiment of FIG. 14.
Figure 20:
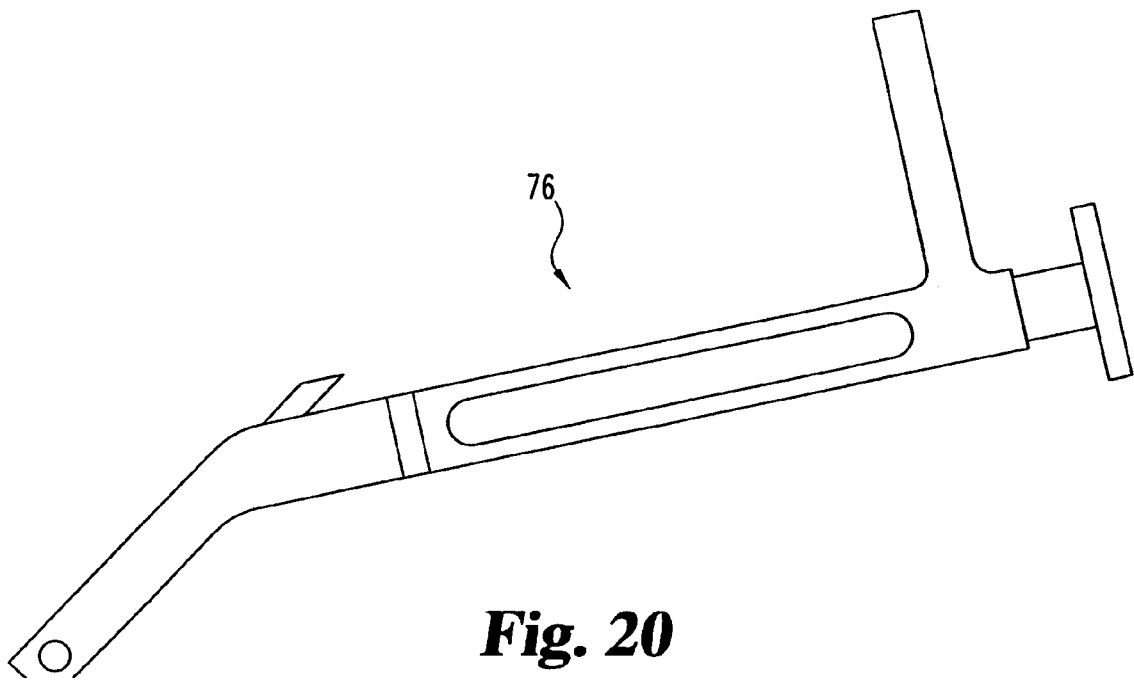
FIG. 20 is a side view of a broach handle used with the present invention.
Figure 21:
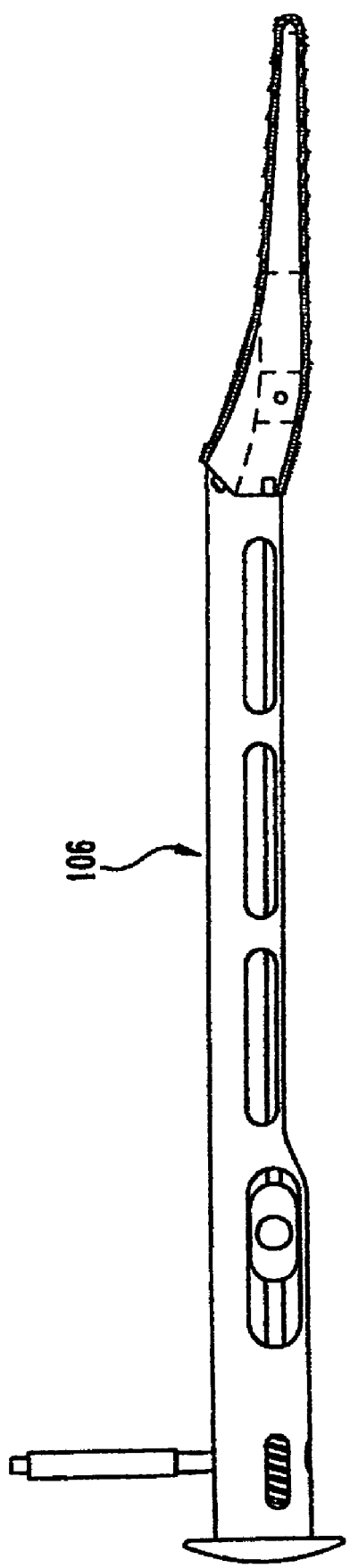
FIG. 21 is a side view of another broach handle used with the present invention.

Different types of broach handles may be used, such as the angled broach handle 76 shown in FIG. 20 and the straight broach handle 106 shown in FIG. 21, to introduce the broach segments into the proximal medullary canal and broach the canal in preparation for receiving the hip stem implant. Broach segment 74, for example, may be attached to a broach handle 76 or 106 with a stationary pin 108 extending at an angle from the broach segment, as shown in FIGS. 17-19, into a cylindrical aperture (not shown) in the distal end of broach handle 76 or 106. Pin 108 may have a transverse groove or detent, and a transverse locking pin may be inserted into a side hole in handle 76 and into the detent in pin 108 to secure the broach segment to the handle. To aid in preventing rotation, a pin may also be provided on the distal end of handle 76 to extend into a mating hole in broach segment 74, preferably on the medial side of pin 108.

Referring again to FIG. 21, handle 106 is a modified form of the Biomet Exact™ broach handle, having extended overall length and a spring-loaded, retractable pin extending from its distal end on an axis substantially parallel to that of the handle. The retractable pin has a length and diameter sufficient for unthreaded insertion into aperture 94 in broach segment 72. The pin in the handle is retracted as pin 108 of broach segment 74 is inserted into the handle's distal end aperture, and is then released into aperture 94 whereby the two pins on different axes cooperate to secure the broach segments to each other and to the handle. A similar coupling mechanism may be provided for attachment of handle 76 if desired.

Broach segments 72 and 74 are assembled as shown in FIGS. 18 and 19. The receiver slot 96 of broach segment 74 is positioned adjacent the receiver portion 82 of broach segment 72 so that broach segment 74 may be slid over the receiver portion 82 as shown in FIG. 18. The rib 92 of the receiver portion 82 also slides into the retention groove 104 of the receiver slot 96. FIG. 19 shows broach segments 72 and 74 fully engaged.

The instrument 70 is assembled and used during a total hip arthroplasty procedure in a similar fashion to that in which the instrument 10 is assembled and used, as previously described and shown in FIGS. 10-13. First, preferably, broach segment 72 is inserted through the posterior incision with the aid of the pusher rod 78, which has a shaft 110 and a threaded end 112 which is screwed into threaded aperture 94 within the proximal end 84 of broach segment 72 for this insertion step. Broach segment 74 is then preferably inserted through the anterior incision, either by hand or with the aid of the broach handle 76. Next, the broach segments are laterally slidably engaged in vivo. If handle 76 is in place, broaching may be performed through the anterior incision by impacting the proximal end of the handle so as to drive the broach head into the canal and then applying a counterforce to the handle to withdraw the broach head. Alternatively, handle 106 may be used to supply broaching action through the posterior incision (with the pusher rod removed). When broaching is completed, instrument 70 is preferably removed and disassembled in reverse order.

Another embodiment of the present invention is an instrument and method for broaching the proximal medullary canal of a femur using a two-incision technique to introduce a single-piece broach head through an anterior incision of a patient while guiding movement of the broach head with a guide shaft inserted through a posterior incision of the patient. The broaching procedure may be performed through the anterior incision using an angled broach handle, as shown in FIG. 22, or through the posterior incision using a straight broach handle as shown in FIG. 23.

Figure 22:
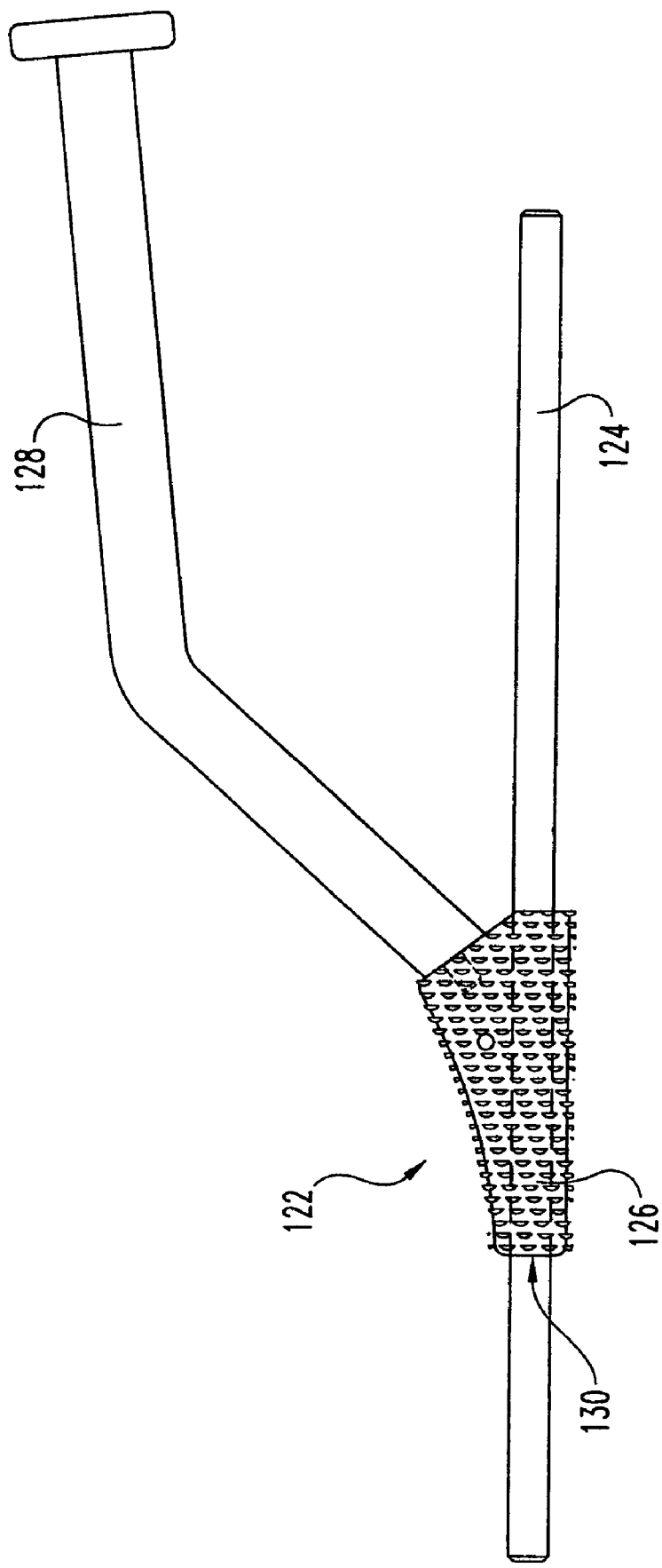
FIG. 22 is a side view of another broaching instrument of the present invention.

Referring to FIG. 22, a broach instrument 122 used to perform the broaching procedure through the anterior incision of the patient generally comprises a guide shaft 124 and a single-piece broach head 126 that may be permanently connected to an angled broach handle 128. The broach head 126 has an axial bore 130 that is sized and shaped for receiving the guide shaft 124 during use. Alternatively, the single-piece broach head 126 may be removably attachable to an angled broach handle such as the angled broach handle 76 shown in FIG. 20.

The method of broaching the canal through the anterior incision generally comprises first inserting the single-piece broach head 126 through the anterior incision and then positioning the broach head 126 within the proximal medullary canal. Next, the guide shaft 124 is then preferably inserted through the posterior incision and aligned with the axial bore 130 of the broach head 126. The guide shaft 124 is then inserted through the axial bore 130 of the broach head and into the canal so that the guide shaft 124 is substantially aligned with the centerline of the canal. The angled broach handle is then attached to the broach head if not previously attached. Finally, the broach head 126 is moved along the guide shaft 124 as the angled broach handle 128 is manipulated through the anterior incision to broach the canal in preparation for receiving the implant.

Figure 23:
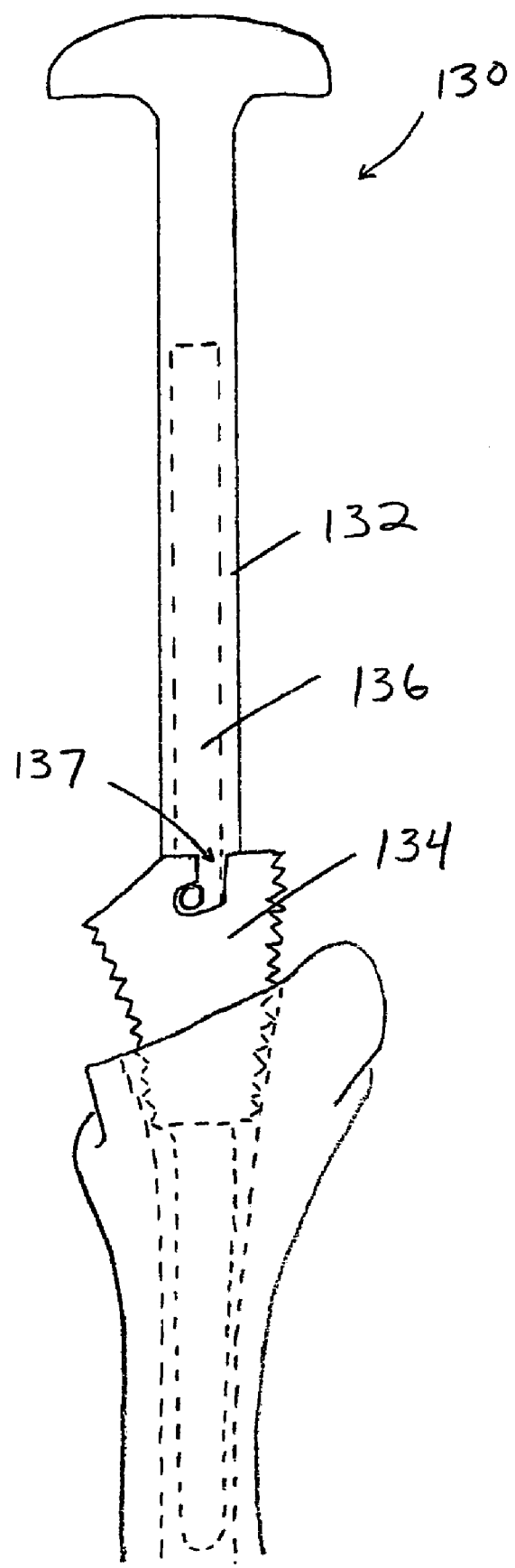
FIG. 23 is a view of another broaching instrument of the present invention.

Alternatively, as shown in FIG. 23, a broaching instrument 130 used to perform the broaching procedure through the posterior incision may comprise a straight broach handle 132 with a single-piece broach head 134 and a guide shaft 136. The broach head 134 may be secured to the broach handle 132 by means of a bayonet mount, e.g., a J-slot connector 137, or a threaded connection (not shown).

The method of broaching the canal through the posterior incision is similar to that described above with respect to FIG. 22, the main difference being that the handle is inserted through the posterior incision. The broach head is inserted through the anterior incision, the guide shaft is inserted through the posterior incision and through the broach head, and the straight broach handle is inserted through the posterior incision and attached to the broach head. The broach head is moved along the guide shaft as the broach handle is manipulated through the posterior incision to broach the canal.

Figure 26:
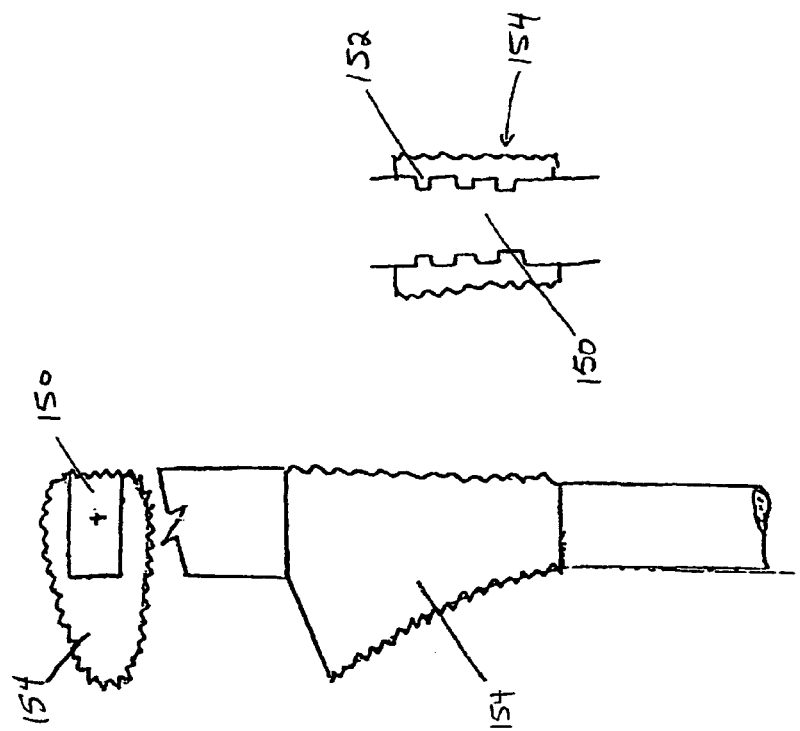
FIG. 26 illustrates an alternative connection for the broaching instrument shown in FIG. 25.
Figure 25:
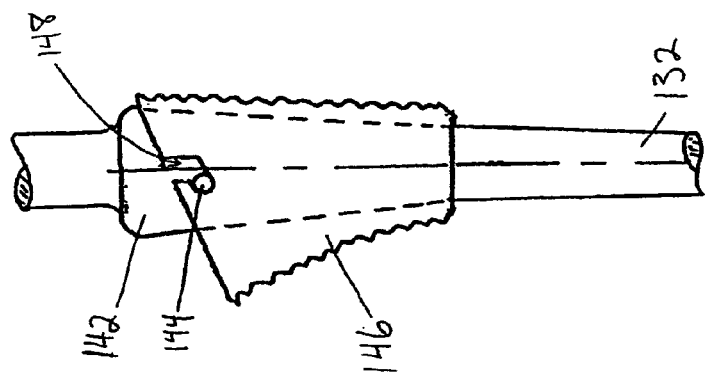
FIG. 25 is a side view of the assembled broaching instrument of FIG. 24.
Figure 24:
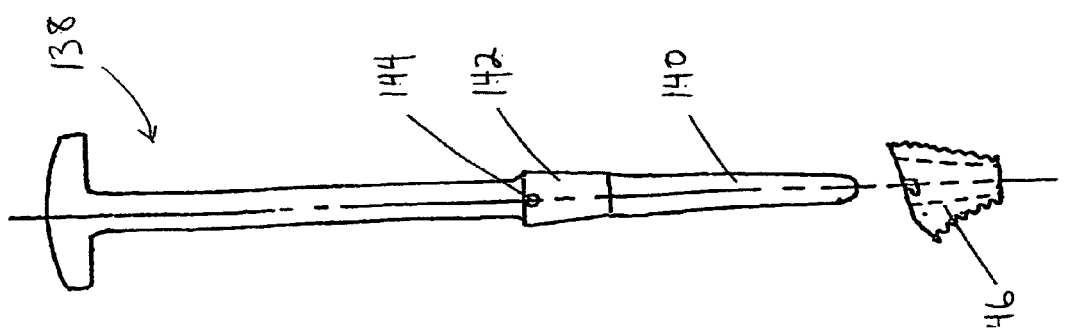
FIG. 24 is an exploded side view of another broaching instrument of the present invention.

As another alternative, the broach handle 138 shown in FIGS. 24 and 25 utilizes a guide tip 140 for guiding the broach handle 138 into the medullary canal during use. The broach handle 138 has a receiver portion 142 with locking pin 144 for receiving the single-piece broach head 146 having a J-slot 148 for receiving the locking pin 144. The broach handle shown in FIG. 26 uses a mortised receiver portion 150 for receiving the tenons 152 of broach head 154. The handle of this embodiment may include broach serrations on its lateral side as can be seen in the top view of FIG. 26.

The method of broaching the canal using the broach handle 138 shown in FIG. 24 generally comprises inserting the broach handle 138 through the posterior incision so that the tip 140 is visualized through the anterior incision. The single-piece broach head 154 is preferably then inserted through the anterior incision and slid over the guide tip 140 so that the single-piece broach head 154 is seated on the receiver portion 142. After connecting the single-piece broach head 154 to the broach handle 138 with the J-slot 148 about the locking pin 144, the guide tip is advanced into the medullary canal in preparation for guiding the broaching action performed through the posterior incision.

In another alternative embodiment to instrument 64, the broach handle may be a solid rod placed through a hollow guide sleeve. The sleeve in this embodiment has an elongated side slot or slots allowing the broach handle to removably engage the single-piece broach head, e.g., by means of one or more spring-loaded pins or other pins extending through the slot(s) and interconnecting the broach handle and broach head. In a further alternative embodiment, the broach handle and guide shaft may both be solid members, arranged parallel to each other during use, with the broach handle attached to one side of the single-piece broach head and the guide shaft extending through the bore in the broach head.

A protective flexible sleeve with shape retaining openings may be used during assembly and use of the previously disclosed broach instruments to protect tissue within the body during a total hip arthroplasty procedure. FIG. 27 shows an embodiment of a flexible sleeve 200 lining a "tunnel" between the posterior incision 202 and anterior incision 204, through the gluteus muscles and other surrounding tissue. The sleeve has a semi-rigid open end 206 that is collapsible, allowing insertion through the posterior incision 202 and advancement through the gluteus muscles and other surrounding tissue, so that the semi-rigid open end 206 may be reopened within the space created by the anterior incision 204 adjacent the femur 208. The sleeve may use flexible wire hoops at each end to hold the ends open. Alternatively, a collapsible and expandable helical scaffold-like structure, such as those used in coronary stents, may be used to provide semi-rigidity throughout the length of the sleeve in addition to the semi-rigidity of the open ends.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A longitudinally split broach head, having a longitudinal bore therethrough, for use in preparing the proximal medullary canal of a femur for receiving a hip stem implant, comprising serrated lateral and medial elongate broach segments having male and female coupling portions, wherein said bore is a through hole that extends longitudinally through a substantial portion of the length of one of said elongate broach segments, wherein said lateral broach segment comprises a male coupling portion and said medial broach segment comprises a female coupling portion, the coupling portions for coupling the lateral and medial broach segments together, the male coupling portion being slidably receivable within the female coupling portion, wherein said bore is within said lateral broach segment, and wherein said female coupling portion is an open curve which surrounds said bore.

2. A broach instrument having a distally tapered longitudinally split broach head for use in preparing the proximal medullary canal of a femur for receiving a hip stem implant, said broach instrument comprising:
   a lateral broach segment having serrations along at least a portion thereof; and
   a medial broach segment having serrations along a distally tapered substantial portion thereof and having a proximal end that is longitudinally slidably engageable with a distal end of said lateral broach segment into an engaged state in which said serrations of said lateral and medial broach segments extend longitudinally alongside each other, exhibiting medial/lateral asymmetry, for a substantial portion of each of their lengths;
   wherein said instrument has a locked configuration in which said medial broach segment is longitudinally fixed with respect to said lateral broach segment.

3. A broach instrument having a distally tapered longitudinally split broach head for use in preparing the proximal medullary canal of a femur for receiving a hip stem implant, said broach instrument comprising:

a lateral broach segment having serrations along at least a portion thereof;

a medial broach segment having serrations along at least a portion thereof and having a proximal end that is longitudinally slidably engageable with a distal end of said lateral broach segment into an engaged state in which said serrations of said lateral and medial broach segments extend longitudinally alongside each other for a substantial portion of each of their lengths;

a bore therethrough for receiving an elongated shaft during use;

wherein said medial and lateral broach segments have a fully assembled configuration in which said broach segments are held together so as to inhibit separate delivery of impact force to said medial and lateral broach segments, whereby said broach segments move as a unit during broaching of said proximal medullary canal.

4. The broach instrument of claim 3, further comprising a handle engaging at least one of said broach segments.

5. The broach instrument of claim 4, wherein said handle is integrally formed with one of said broach segments.

6. A longitudinally split broach head, having a longitudinal bore therethrough, for use in preparing the proximal medullary canal of a femur for receiving a hip stem implant, comprising serrated lateral and medial elongate broach segments having male and female coupling portions and respective longitudinal axes aligned with said longitudinal bore when said broach segments are coupled together, wherein said longitudinal bore is a through hole that extends longitudinally through a substantial portion of the length of one of said elongate broach segments, wherein the coupling portions are for coupling the lateral and medial broach segments together, the male coupling portion being slidably receivable within the female coupling portion, wherein said bore is within said lateral broach segment, and wherein said female coupling portion is an open curve which surrounds said bore.

7. The longitudinally split broach head of claim 6, wherein said bore is within said lateral broach segment.

8. The longitudinally split broach head of claim 7, wherein said female coupling portion surrounds said bore.

9. The longitudinal split broach head of claim 6, wherein one of said respective longitudinal axes is coaxial with said longitudinal bore.

10. The broach instrument of claim 3, further comprising an elongate shaft sized to fit through said bore and a cutting end having a plurality of flutes, said cutting end coupled to said elongate shaft.

11. The broach instrument of claim 3, further comprising an elongate guide shaft sized to fit through said bore.

12. The broach instrument of claim 11, further comprising a reamer coupled to said elongate shaft.

13. The broach instrument of claim 12, wherein said reamer is distally tapered.

14. The broach instrument of claim 13, wherein said reamer has a proximal end cross-section that is substantially the same size as a distal end cross-section of said broach head.

15. The longitudinally split broach head of claim 1, wherein said medial and lateral broach segments have a fully assembled configuration in which said broach segments are held together so as to inhibit separate delivery of impact force to said medial and lateral broach segments, whereby said broach segments move as a unit during broaching of said proximal medullary canal.

16. The longitudinally split broach head of claim 15, further comprising an elongate shaft adapted to extend through said longitudinal bore, and retaining means cooperating with said shaft for holding said broach segments together so as to inhibit separate delivery of impact force to either broach segment.

17. The longitudinally split broach head of claim 1, wherein said longitudinal bore has a longitudinal axis extending through said female coupling portion when said broach head is assembled.

18. The broach instrument of claim 2, wherein said longitudinally split broach head has a longitudinal axis extending through the distal ends of both broach segments, and wherein said tapered serrated portion of said medial broach segment extends away from said longitudinal axis more than said lateral broach segment.

19. The broach instrument of claim 18, wherein said medial and lateral broach segments are laterally fixed with respect to said longitudinal axis.

20. The broach instrument of claim 2, further comprising an elongate shaft and retaining means cooperating therewith for holding said broach segments together so as to inhibit separate delivery of impact force to either broach segment.

21. The broach instrument of claim 2, wherein said instrument has a fully assembled configuration in which said broach segments are held together so as to inhibit separate delivery of impact force to said medial and lateral broach segments, whereby said broach segments move as a unit during broaching of said proximal medullary canal.

22. The longitudinally split broach head of claim 1, wherein said medial broach segment of said longitudinally split broach head has serrations on a distally tapered portion thereof.

23. The longitudinally split broach head of claim 22, wherein said tapered serrated portion of said medial broach segment is curved away from said longitudinal bore in the proximal direction.

24. The longitudinally split broach head of claim 23, wherein said broach segments each have a cross-cut serrated surface.

25. The longitudinally split broach head of claim 24, wherein said lateral and medial broach segments are detachably engageable and have an engaged state in which their serrated surfaces are substantially coextensive longitudinally and have a longitudinal seam therebetween.

26. The longitudinally split broach head of claim 1, wherein said medial broach segment of said longitudinally split broach head has serrations on a distally tapered portion thereof.

27. The longitudinally split broach head of claim 26, wherein said tapered serrated portion of said medial broach segment is curved away from said longitudinal bore in the proximal direction.

28. The longitudinally split broach head of claim 27, wherein said broach segments each have a cross-cut serrated surface.

29. The longitudinally split broach head of claim 28, wherein said lateral and medial broach segments are detachably engageable and have an engaged state in which their serrated surfaces are substantially coextensive longitudinally and have a longitudinal seam therebetween.

30. The longitudinally split broach head of claim 6, wherein said medial broach segment of said longitudinally split broach head has serrations on a distally tapered portion thereof.

31. The longitudinally split broach head of claim 30, wherein said tapered serrated portion of said medial broach segment is curved away from said longitudinal bore in the proximal direction.

32. The longitudinally split broach head of claim 31, wherein said broach segments each have a cross-cut serrated surface.

33. The longitudinally split broach head of claim 32, wherein said lateral and medial broach segments are detachably engageable and have an engaged state in which their serrated surfaces are substantially coextensive longitudinally and have a longitudinal seam therebetween.

34. The longitudinally split broach head of claim 8, wherein said medial broach segment of said longitudinally split broach head has serrations on a distally tapered portion thereof.

35. The longitudinally split broach head of claim 2, wherein said tapered serrated portion of said medial broach segment is curved away from said lateral broach segment in the proximal direction.

36. The longitudinally split broach head of claim 35, wherein said broach segments each have a cross-cut serrated surface.

37. The longitudinally split broach head of claim 36, wherein said lateral and medial broach segments are detachably engageable and have an engaged state in which their serrated surfaces are substantially coextensive longitudinally and have a longitudinal seam therebetween.

38. The longitudinally split broach head of claim 1, wherein said longitudinal bore has a closed curve transverse cross-section.

39. The longitudinally split broach head of claim 6, wherein said longitudinal bore has a closed curve transverse cross-section.

* * * * *